(12) United States Patent
Lemmens (10) Patent No.: US 7,659,392 B2
(45) Date of Patent: *Feb. 9, 2010

(54) METHOD OF SEPARATION USING AROMATIC THIOETHER LIGANDS

(75) Inventor: Raf Lemmens, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 1090 days.

This patent is subject to a terminal disclaimer.

(21) Appl. No.: 10/504,884

(22) PCT Filed: Feb. 14, 2003

(86) PCT No.: PCT/SE03/00257

§ 371 (c)(1),
(2), (4) Date: Aug. 13, 2004

(87) PCT Pub. No.: WO03/070944

PCT Pub. Date: Aug. 28, 2003

(65) Prior Publication Data

US 2005/0080251 A1 Apr. 14, 2005

(30) Foreign Application Priority Data

Feb. 21, 2002 (SE) .................................. 0200543

(51) Int. Cl.
*C07H 21/02* (2006.01)
(52) U.S. Cl. ..................................................... 536/25.4
(58) Field of Classification Search ................. 536/25.4
See application file for complete search history.

(56) References Cited

U.S. PATENT DOCUMENTS 4,696,980 A * 9/1987 Porath ..................... 525/326.1

FOREIGN PATENT DOCUMENTS

| WO | WO 92/16292 | * 10/1992 |
| WO | WO 95/33557 | 12/1995 |
| WO | WO 00/73318 | 12/2000 |
| WO | WO 01/37987 | 5/2001 |
| WO | WO 01/38227 | 5/2001 |

OTHER PUBLICATIONS

Prazares et al, Analytical Biochemistry, 1999, 275, 122-124.*
G. Ferreira, et al., "Downstream processing of plasmid DNA for gene therapy and DNA vaccine applications", *Tibtech*, vol. 18, Sep. 2000, p. 380-388.
J. Porath, et al., "Thiophilic adsorption—a new method for protein fractionation", *FEBS*, vol. 185, No. 2, Jun. 1985, p. 306-310.
M. Diogo, et al., "Separation and Analysis of Plasmid Denatured Forms Using Hydrophobic Interaction Chromatography", *Analytical Biochemistry*, vol. 275, May 1999, p. 122-124.

* cited by examiner

*Primary Examiner*—Shaojia Anna Jiang
*Assistant Examiner*—Ganapathy Krishnan
(74) *Attorney, Agent, or Firm*—Yonggang Ji (57) ABSTRACT

The present invention is a method of separating nucleic acid molecules from contaminants, such as proteins, in a solution and isolating one or more desired nucleic acid molecules, which method comprises the following steps (a) providing an aqueous adsorption solution, which includes nucleic acids and a salt that forms lyotropic ions when dissolved; (b) passing said solution over a matrix to adsorb the nucleic acids onto the matrix, said matrix including an aromatic ring moiety and at least one thioether moiety; (c) passing an aqueous eluent over said matrix to desorb the nucleic acid molecules therefrom, which eluent includes a salt that forms lyotropic ions and a gradient of increasing ionic strength originating from an increasing concentration of a salt that forms less lyotropic ions when dissolved than the ones present in said aqueous adsorption solution; and (d) isolating a fraction comprising the desired nucleic acid molecules.

10 Claims, 14 Drawing Sheets

METHOD OF SEPARATION USING AROMATIC THIOETHER LIGANDS

CROSS REFERENCE TO RELATED APPLICATIONS

This application is a filing under 35 U.S.C. § 371 and claims priority to international patent application number PCT/SE03/00257 filed Feb. 14, 2003, published on Aug. 28, 2003 as WO 03/070944 and also claims priority to patent application number 0200543-7 filed in Sweden on Feb. 21, 2002; the disclosures of which are incorporated herein by reference in their entireties.

TECHNICAL FIELD

The present invention relates to separation of nucleic acid molecules, especially plasmids, from other components in a solution. The method utilises aromatic thioether ligands for adsorption of the nucleic acid molecules and provides a novel scheme of desorbing the adsorbed molecules, which greatly improves the separation efficiency of the method all in all. The present method is preferably a chromatographic process.

BACKGROUND

In the last decade, the administration of therapeutic genes to patients has become a reality for preventing or treating various diseases. Non-viral vectors are often preferred in clinical applications to minimise the risk of viral infections. This increases the demand for highly purified plasmids for use in gene therapy and plasmid-based vaccines. The stringent guidelines and rules set forth by health authorities require homogeneous preparations of purified supercoiled plasmid DNA for clinical applications.

Chromatography is the method of choice for both small- and large-scale purification of supercoiled plasmid DNA (Ferreira, G. N. M., Prazeres, D. M. F., Cabral, J. M. S., and Schleef, M. Plasmid manufacturing—An overview. In: Schleef, M. (Ed.) *Plasmids for therapy and vaccination* Wiley-VCH: Weinheim, 2001, p. 193-236). Separation methods based on size-exclusion, ion-exchange and hydrophobic interaction chromatography (HIC) have been shown to be suitable for purifying plasmid DNA (Ferreira, G. N. M., Monteiro, G. A., Prazeres, D. M. F., and Cabral, J. M. S. Downstream processing of plasmid DNA for gene therapy and DNA vaccine applications. *TIBTECH* 2000; 18, 380-388). Affinity chromatography, which is based on sequence-specific interactions between an immobilised synthetic oligonucleotide and a stretch of the plasmid DNA, has also been suggested (Schluep, T., and Cooney, C. L. Purification of plasmids by triplex affinity interaction. *Nucleic Acids Research* 1998; 26, 4524-4528). However, none of these techniques results in a homogeneous preparation of supercoiled plasmid DNA in sufficient quantities for non-analytical applications.

To circumvent this problem, efforts in the past were directed towards the development of sample preparation techniques that would minimise the formation of nicked forms of plasmid DNA. However, this approach was difficult to reproduce and the quality of the plasmid DNA thus produced did not meet the stringent specifications set forth for the final product (Levy, M. S., O'Kennedy, R. D., Ayazi-Shamlou, P., and Dunnill, P. Biochemical engineering approaches to the challenges of producing pure plasmid DNA. *Trends in Biotechnology* 2000; 18, 296-305). Accordingly, there has been a recognised need for developing a new and robust separation protocol for supercoiled plasmid DNA that would significantly reduce the tedious efforts for optimisation of the upstream processes.

Oscarsson et al. suggested thiophilic chromatography (Oscarsson, S., and Porath, J. Covalent chromatography and salt-promoted thiophilic adsorption. *Analytical Biochemistry* 1989; 176, 330-337; Porath, J., Maisano, F., and Belew, M. Thiophilic adsorption—a new method for protein fractionation. *FEBS Letters* 1985; 185, 306-310) to protein purification. In a patent application of later date, WO 95/33557, Oscarsson and Porath disclose an alkali-resistant protein adsorbent, which is similar to the ones discussed in 1989, but wherein the thiophilic group has been distanced from the rest of the ligand to improve the properties in alkaline environments. Adsorption of proteins is favoured by high concentrations of lyotropic salt, and desorption is achieved using the conditions conventionally used in hydrophobic interaction chromatography (HIC), which is to replace the lyotropic salt by another, less lyotropic salt or simply by water.

More recently, the ability of different ligand structures comprising thioethers to bind the different isoforms of plasmid DNA under conditions that would be applicable in large-scale processes have been investigated. This was disclosed in Swedish patent application SE 0101380.4, which however was not published at the time of the filing of the present application. Accordingly it was possible to narrow down the specific structures that are required for an "optimal ligand" to interact with supercoiled plasmid DNA and purify it selectively. As a result, a new group of thiophilic ligands, namely aromatic thioethers, have been identified, which effectively differentiates between the isoforms of plasmid DNA. Media comprising these ligands have been shown to efficiently separate supercoiled (covalently closed circular (ccc)) plasmid DNA from its isoform, i.e. open circular (oc) form in a single chromatography step. Accordingly, the use of these media appears to be promising and should facilitate the production of highly purified supercoiled plasmid DNA for use in gene therapy and DNA vaccine applications.

However, even though plasmid DNA can be separated from its isoform, other problems remain to be solved. For example, a cell lysate comprising a desired nucleic acid will usually also comprise one or more proteins, such as enzymes, or various degradation products. Even though previously reported methods in principle are capable of separating protein from desired nucleic acids, the resolution obtained is still not fully satisfactory for an efficient production process. Cell lysates that comprise deoxynucleic acid (DNA) will normally also comprise ribonucleic acid (RNA) and some remaining proteins. However, in the above discussed context when plasmid DNA is desired for pharmaceutical purposes, both will constitute contaminants that has to be removed. Furthermore, chromatographic purification of plasmid DNA results in most cases in co-purification of endotoxins, i.e. membrane components of host bacteria, that have to be removed to fulfil the rigorous requirements for pharmaceutical products. Accordingly, there is a need of improvements of the presented purification protocols using thiophilic chromatography as regards the separation of nucleic acids from the above-discussed contaminants.

SUMMARY OF THE PRESENT INVENTION

One object of the present invention is to provide an alternative method of separating nucleic acids, such as DNA, from a solution using a matrix comprising one or more aromatic thioether ligands. This and other objects can be achieved by the method disclosed in the appended claims.

A more specific object of the present invention is to provide a method of desorbing molecules bound to such matrices, which method provides a more efficient separation of the plasmids from one or more undesired components, such as proteins, RNA, and/or endotoxins.

Another object of the invention is to provide a method of desorbing as mentioned above, which also is capable of separating different plasmid isoforms from each other, more specifically ccc plasmid DNA from oc plasmid DNA.

Definitions

The term "proteineous" as used herein includes whole protein as well as parts or traces of protein and other molecules comprising a peptidic structure.

The term "nucleic acid molecules" is used herein synonymously with the term "nucleotides" and includes DNA, e.g. plasmids, such as open circular (oc or nicked) plasmid DNA, supercoiled (ccc) plasmid DNA and other DNA, such as genomic. DNA, as well as RNA, such as mRNA, tRNA and sRNA.

The phrase to "pass a solution/eluent over a matrix" means any way of contacting a matrix with a solution or eluent as well as removal thereof after a certain period of time. Accordingly, the term includes dynamic chromatographic methods as well as batch procedures.

The term "eluent" is used herein in its conventional meaning in chromatography, i.e. a solution capable of perturbing the interaction between the solid phase (adsorbent matrix) and product (nucleic acid molecules) and promoting selective dissociation of the product from the solid phase.

The term "lyotropic" is a measure of the ability of ions to influence the hydrophobic character of the interactions in a solvent.

BRIEF DESCRIPTION OF THE DRAWINGS

FIG. 9 shows chromatograms illustrating the difference in endotoxin profile when comparing decreasing salt elution (FIG. 9a) with increasing salt elution (FIG. 9b).

DETAILED DESCRIPTION OF THE PRESENT INVENTION

More specifically, a first aspect of the present invention is a method of separating nucleic acid molecules from contaminants in a solution, which method comprises the following steps (a) providing an aqueous adsorption solution, which comprises nucleic acids and a salt that forms lyotropic ions when dissolved;

(b) passing said solution over a matrix to adsorb the desired nucleic acids onto the matrix, which comprises an aromatic ring moiety and at least one thioether moiety;

(c) optionally washing the matrix;

(d) passing an aqueous eluent over said matrix to desorb the nucleic acid molecules therefrom, which eluent in addition to a salt that forms lyotropic ions also comprises a gradient of increasing ionic strength originating from an increasing concentration of salt that forms less lyotropic ions when dissolved than the ones present during adsorption; and (e) isolating the fraction comprising the desired nucleic acid molecules.

In the most preferred embodiment, the ions referred to in steps (a) and (d) are the anions formed as each respective salt is dissolved.

The method according to the invention can be used to isolate nucleic acid molecules expressed in cells, for example in recombinant cells. Consequently, it also comprises a first step of disintegrating the cells to provide the solution comprising nucleic acid molecules. Such disintegration is performed e.g. by lysis, such as alkaline lysis, according to standard protocols (see e.g. Maniatis, T, Fritsch, E. F. and Sambrook, J. (1982) Molecular Cloning: A Laboratory Manual, Cold Spring Harbour Laboratory Press, Cold Spring Harbour, N.Y.). Accordingly, the solution provided in step (a) above is preferably essentially free of cell debris. In addition, the present invention is also useful for analysis of nucleotide mixtures in solution, i.e. a separation for analytical purposes.

In an advantageous embodiment of the present method, the fraction isolated according to step (e) is plasmid DNA, which is essentially free from RNA. As discussed above, this is a strict requirement in pharmaceutical preparations. As will be shown in the experimental part below, the RNA maintains firmly bound to the matrix during the elution of DNA. If desired, the RNA can then easily be removed by washing the matrix with water or low salt buffer, e.g. for regeneration of the matrix. However, in an alternative embodiment, the present invention is a method whereby RNA is recovered, e.g. for scientific research, from a solution that also comprises DNA. Both these embodiments exhibit the clear and unexpected advantage of separating nucleic acid molecules not only from each other, but also from contaminants, such as proteineous components and endotoxins, present in a solution. As will be shown in the experimental part, protein that binds to the matrix used according to the present invention are eluted at a different stage than the nucleic acids, and can accordingly be collected in a separate fraction.

The present invention shows that it is possible to separate both proteineous components and RNA from the DNA in a cell lysate by use of a novel principle of elution from matrices comprising aromatic thioether ligands. In addition, the present method has also been shown to efficiently separate a desired nucleic acid molecule from other contaminants, such as endotoxins. Accordingly, the method according to the invention is useful e.g. for purification of nucleic acids for use in gene therapy, DNA vaccines and laboratory studies related to gene therapy. In an advantageous embodiment, the present method will provide isolated supercoiled plasmid DNA of acceptable gene therapy grade. As mentioned above, the previously described methods for isolation of such carriers have not been satisfactory to this end.

In one embodiment of the present method, the solution provided in step (a) comprises a dissolved alkali salt, such as ammonium sulphate or sodium sulphate. Accordingly, the anions present therein during the adsorption will be the strongly lyotropic sulphate ions. In a specific embodiment, the concentration of said salt is below about 3.0 M, such as about 2.5 M. As the skilled person in this field will realise, the upper limit is determined by the solubility of each salt. However, as the skilled in this field will realise, different salt concentrations may be required in different situations, not only depending on the specific ligand used on the matrix, but also on the nucleic acid to be separated. The pH of the solution during adsorption step can differ from the one during the elution step. However, to assure the stability of the nucleic acids to be separated, the pH should remain at physiological pH, i.e. in the range of about 6.5-8.5.

In an advantageous embodiment, the matrix to which the desired nucleic acids have been adsorbed is washed before elution according to step (d). During washing, loosely bound contaminants are removed. Such washing can easily be performed by the skilled in this field according to standard procedures.

Step (d) according to the present invention is performed with a suitable aqueous eluent, which in addition to a salt that forms lyotropic ions also comprises a gradient of increasing ionic strength, for example a continuous gradient. However, for certain purposes as large-scale production of supercoiled plasmid DNA, it may be desired to use a step-wise gradient.

The increasing ionic strength of the eluent used in step (d) is provided by an increasing concentration of a salt in the eluent, which salt is capable of forming less lyotropic ions, such as anions, than the one dissolved in the adsorption solution. As is well known to the skilled in this field, the lyotropic properties of ions can be rated according to the Hofmeister or lyotropic series. The dissolved salt will gradually change the conditions in the solvent, which change was found by the present inventor to be useful to desorb DNA, and RNA as easily separated fractions. In fact it was found that for most ligands, RNA is eluted as the last fraction simply by addition of water. Proteins and endotoxins can only be removed by the addition of water, indicating a solely hydrophobic binding mechanism of these molecules to the matrix, completely different from the mechanisms nucleic acids deploy. In one embodiment, the salt dissolved in the eluent is an alkali salt, such as sodium or potassium chloride. Thus, the less lyotropic anions are chloride ions. In a specific embodiment, the maximum concentration of the salt is about 3 M. However, as mentioned above in relation to the salt dissolved in the adsorption solution, for each specific ligand and desired nucleic acid, some routine testing may be needed in order to determine optimal conditions. Similar to the adsorption step, the pH value during elution should be kept in the range where the nucleic acids are stable.

Thus, the present invention is based on the unexpected finding, that nucleic acids adsorbed to a matrix via aromatic thioether ligands can efficiently be eluted by a gradient of increasing ionic strength as discussed above. More specifically, the eluent is comprised of a salt that forms lyotropic ions, such as the buffer used in the adsorption step, and in addition to that a gradient of increasing ionic strength. This is quite contrary to the recently introduced use of aromatic thioether ligand matrices, such as in the above-discussed WO 95/33557, wherein elution was performed by removing the lyotropic salt from the elution buffer. Thus, in the prior ark, elution of aromatic thioether has been performed either by adding an aqueous solution, which dilutes the lyotropic salt, or by adding a salt that replaces the lyotropic salt. In other words, the total salt concentration has been reduced or kept at a similar value during elution. However, the present inventor is the first to show that elution of aromatic thioether ligands can be performed by use of the same buffer as used in the adsorption supplemented with a gradient of increasing ionic strength.

As regards the matrix used in the present method, it is comprised of a ligand as discussed in more detail below coupled to a support via a thioether bond. Each matrix may comprise one or more ligand structures.

In one embodiment, the ligand used comprises an aromatic thioether wherein the aryl group is selected from pyridyl, phenyl, benzyl, toluyl, phenethyl, naphtyl, imidazolyl, pyrazolyl, pyrazinyl, pyrimidinyl pyridazinyl, piperidinyl, morpholinyl, piperazinyl, indolyl quinolinyl and purinyl groups.

Figure 1:
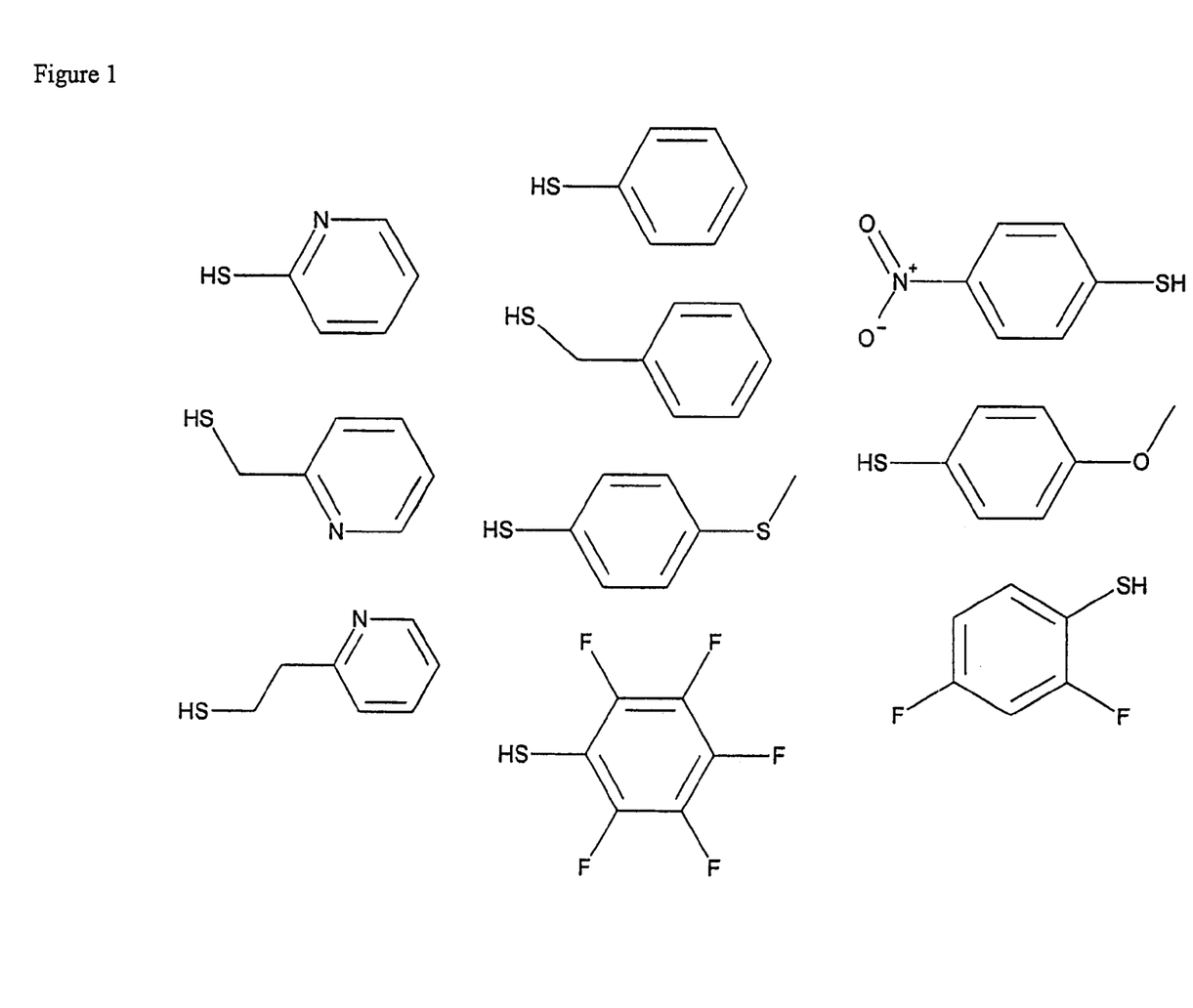
FIG. 1 shows examples of aromatic thioether ligands, which possess separation properties and hence are useful according to the invention.

In an advantageous embodiment, the pyridyl-S and/or phenyl group comprises further substituents on the aryl group, for example as illustrated in FIG. 1.

The ligand attached to the carrier material to form the matrix of the invention can be a mercapto-pyridine, mercaptoalkylpyridine. Hereby it is the mercapto-group that is attached to the carrier material via a thioether binding. Further, as mentioned above, aryl groups forming part of the ligand can be phenyl, benzyl toluyl, phenethyl, naphtyl, imidazolyl, pyrazolyl, pyrazinyl pyrimidinyl, pyridazinyl, piperidinyl, morpholinyl piperazinyl, indolyl, quinolinyl purinyl. Further substituents can also be added on the aromatic ring. By providing the present aromatic thioether ligands with additional substituents, a large range of different separation media can be designed. The substituents can for example be one or more amine groups, nitro groups, ether groups, thiol groups and/or halogens, such as fluorine. These additional substituents can also comprise further carbon atoms, as desired. Also, as the skilled in this field will realise, carbon atoms can be exchanged for heteroatoms in the above discussed ring structures. It is to be understood herein that the term "aromatic thioether ligand" comprises a large range of compounds that can be substituted to a desired extent, some of which will be exemplified below in FIG. 1. The ligand density can be 10-500 μmole/mL carrier, preferably in the range 10-100 μmole/mL carrier.

The matrix used in the present invention comprises ligands that may be of one the same or different chemical structures, coupled to a support. The support can be in any suitable form, such as essentially spherical particles, membranes, filters, microtiter plates etc. The support can be any suitable, well-known inorganic or organic material. Examples of inorganic support materials are glass, silica, or other inert particulate minerals. Examples of organic support materials are agarose, dextran, divinylbenzene etc. There are many commercial products available based on different resins or polymer, e.g. agarose or cross-linked agarose (such as Sepharose™, Amersham Biosciences, Uppsala, Sweden), dextran (such as Sephadex™, Amersham Biosciences, Uppsala, Sweden), polystyrene/divinylbenzene (MonoBeads™, SOURCE™, Amersham Biosciences, Uppsala, Sweden), coated polystyrene, acrylic polymer, dextran acrylic polymer (Sephacryl™, Amersham Biosciences, Uppsala, Sweden), vinylic grafted polymer, or vinylic polymer, different silica based resins such as silica-dextran, silica-acrylic polymer and silica-polyethyleneimine. In an advantageous embodiment, the matrix is cross-linked agarose, which for example may have been functionalised with ligands using epoxy-activation.

The present process may be performed with the matrix arranged in the form of an expanded bed or a packed bed, and can be dynamic, i.e. chromatography, or run in a batch mode. In packed bed adsorption, the matrix is packed in a chromatographic column and all solutions used during a purification process are passed through the column, usually in the same direction. In expanded bed adsorption however, the matrix is expanded and equilibrated by applying a liquid flow through the column, usually from beneath. A stable fluidised expanded bed is formed when there is a balance between particle sedimentation or rising velocity and the flow velocity during application of the sample and washing steps. In the elution step of an expanded bed, the matrix is precipitated and behaves like a packed bed matrix.

In one embodiment, the matrix particles are of a mean size in the range of about 10-300 µm, e.g. within a range of 10-20, 20-50, 50-100, 100-200 or 200-300 µm. However, the particles can advantageously be prepared in any size for which commercially available sieve equipment is available, such as 250, 212, 180, 150, 125, 106, 90, 75, 63, 45, 37, 30, 25, 20, 15 µm.

DETAILED DESCRIPTION OF THE DRAWINGS

FIG. 1 shows examples of a variety of aromatic thioether compounds reacted with Sepharose™ 6 Fast Flow (Amersham Biosciences, Uppsala, Sweden). As appears from this drawing, the aromatic thioether compounds can be provided with different substituents, each of which can result in binding and elution properties that may prove advantageous for different purposes.

Figure 2:
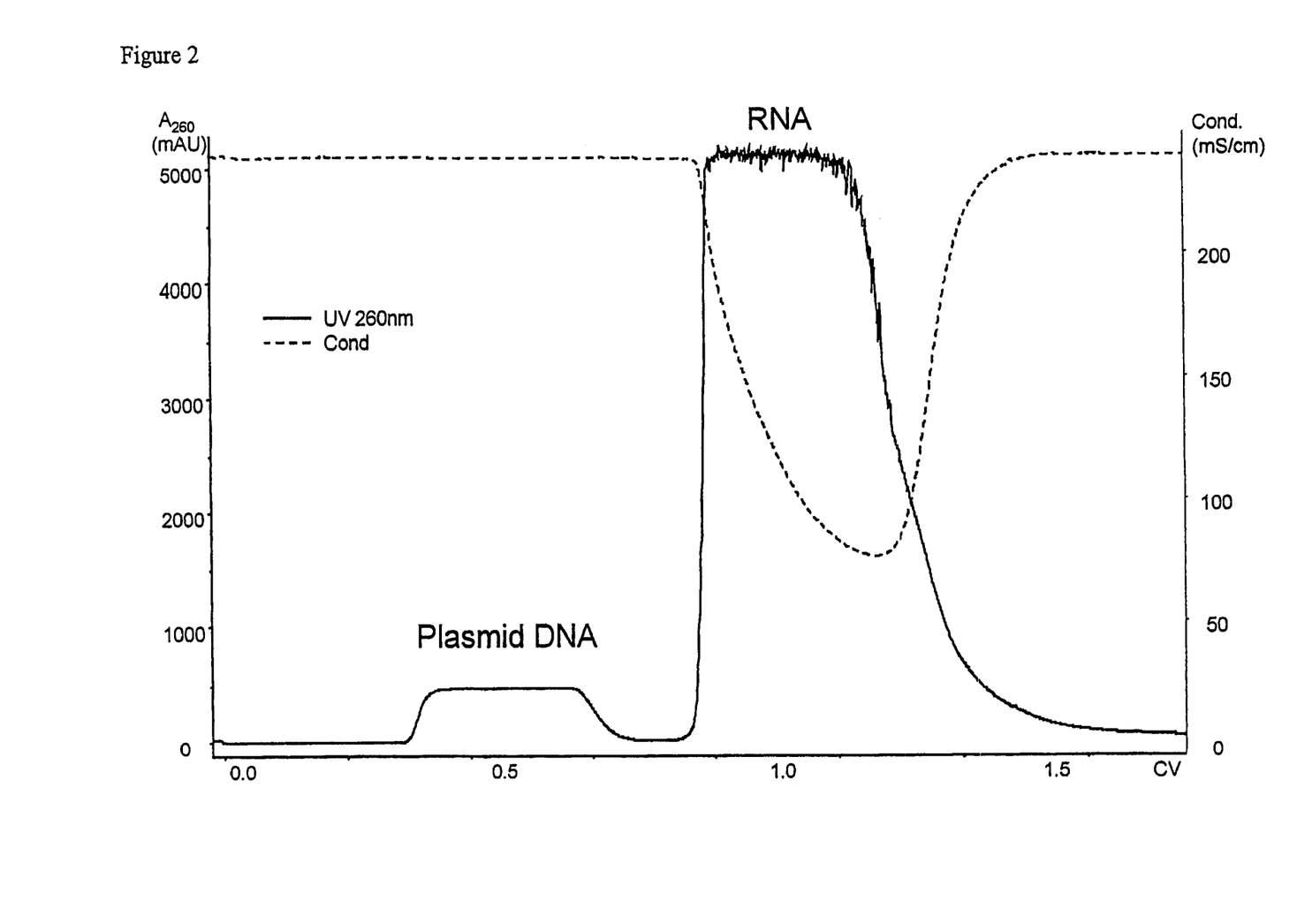
FIG. 2 shows a chromatogram obtained after group separation of alkaline lysate, resulting in separate plasmid DNA and RNA fractions.

FIG. 2 illustrates preparation of plasmid DNA. Alkaline lysate is loaded on a Sepharose™ 6 Fast Flow (Amersham Biosciences, Uppsala, Sweden) column preconditioned in 2.0 M $(NH_4)_2SO_4$, 10 mM EDTA, 100 mM Tris-HCl, pH 7.0. After chromatography at 30 cm/h, plasmid DNA is separated from RNA. Furthermore, plasmid DNA can now be collected in the buffer required for further experiments with thiophilic aromatic chromatography.

Figure 3A:
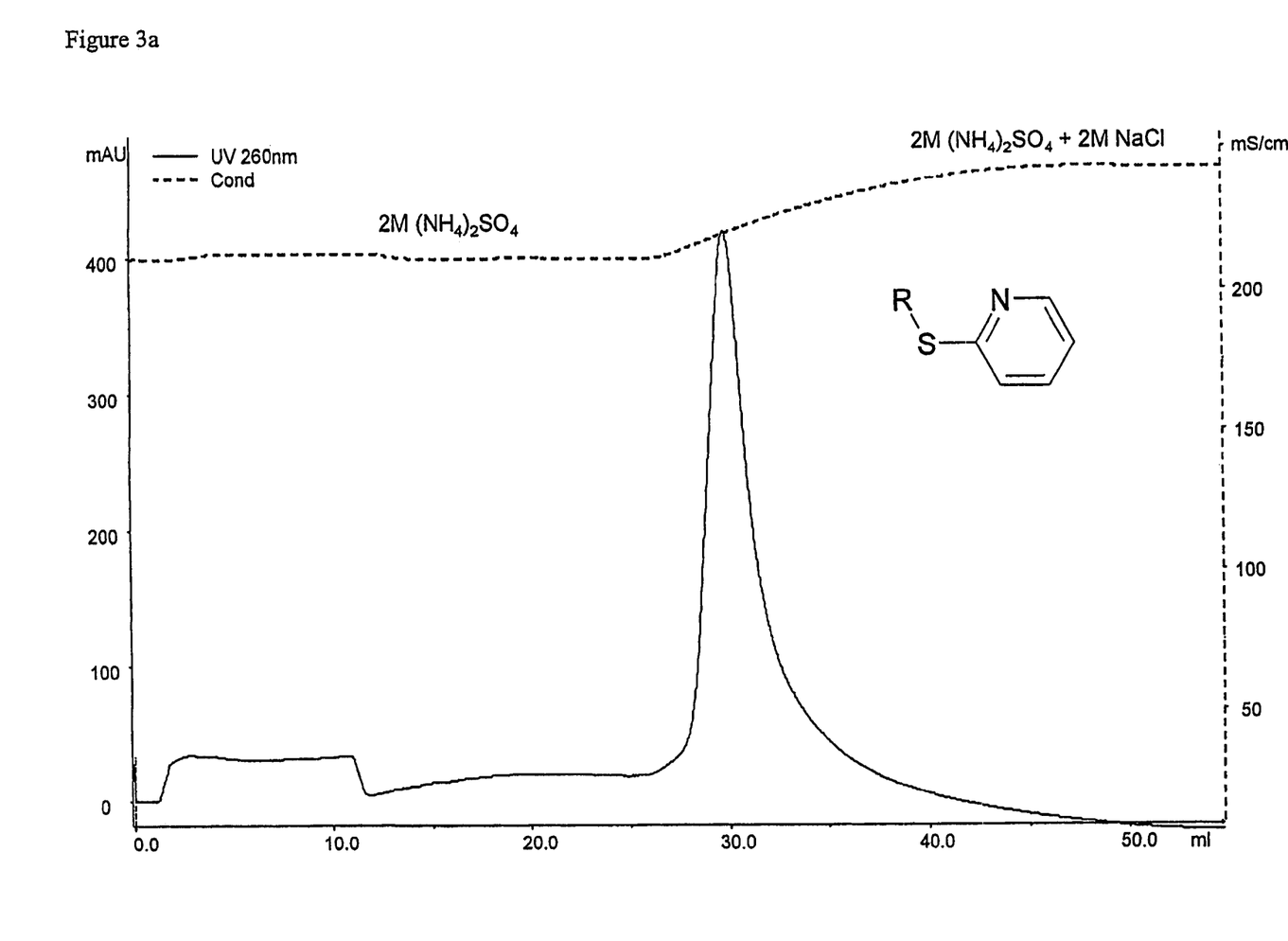
FIG. 3a-d shows results obtained after chromatography on the ligands depicted in the inserts.
Figure 3B:
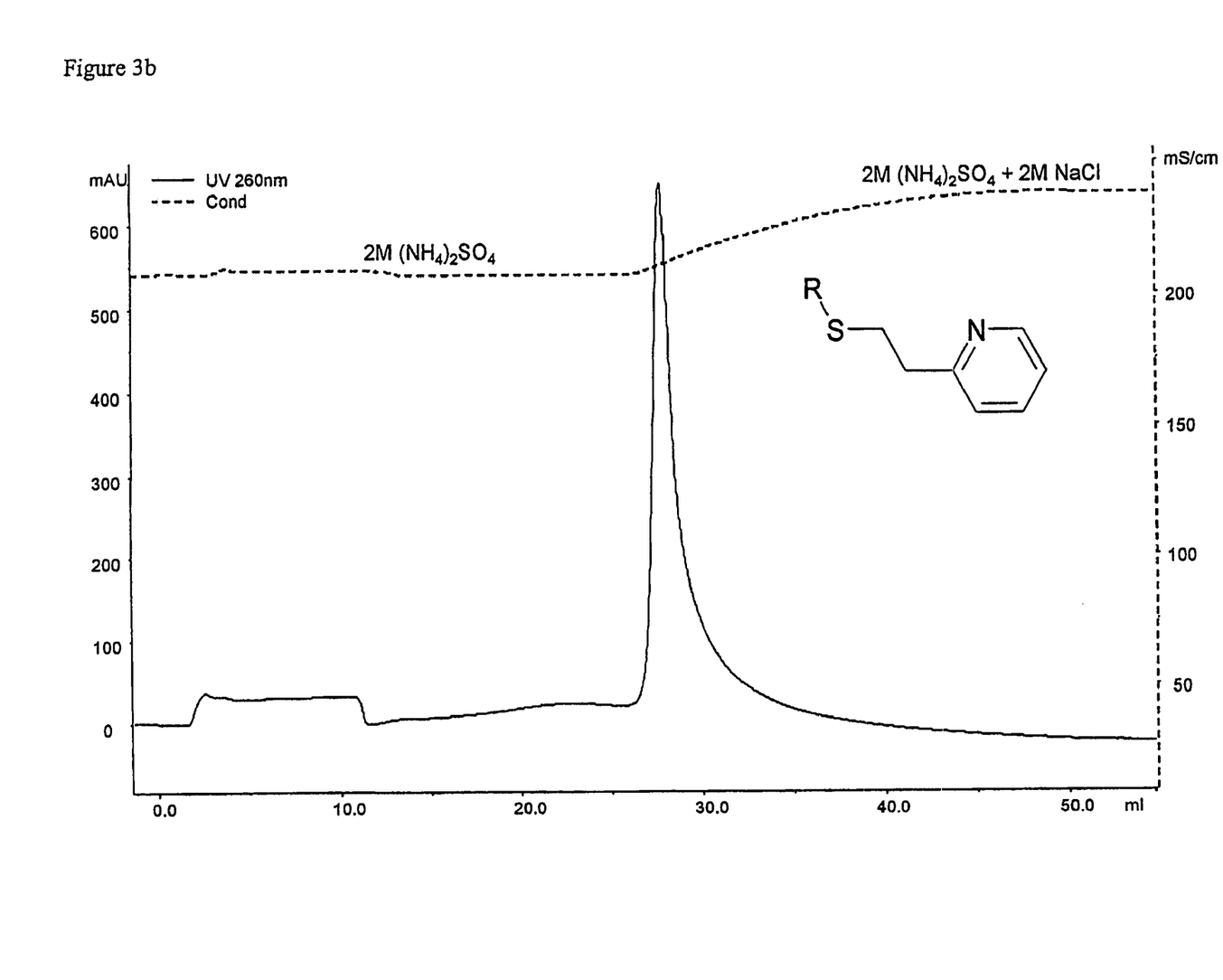
Figure 3C:
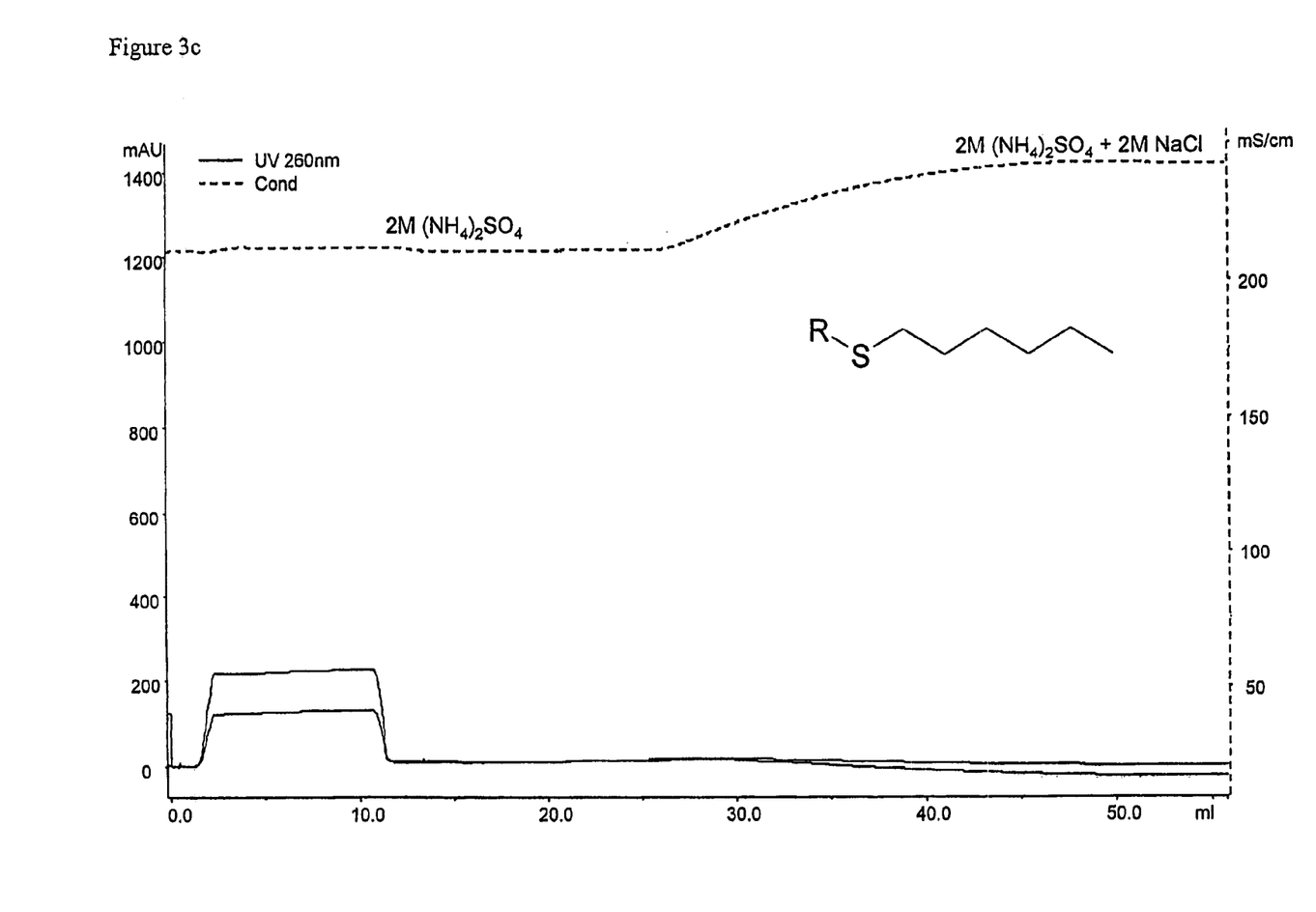
Figure 3D:
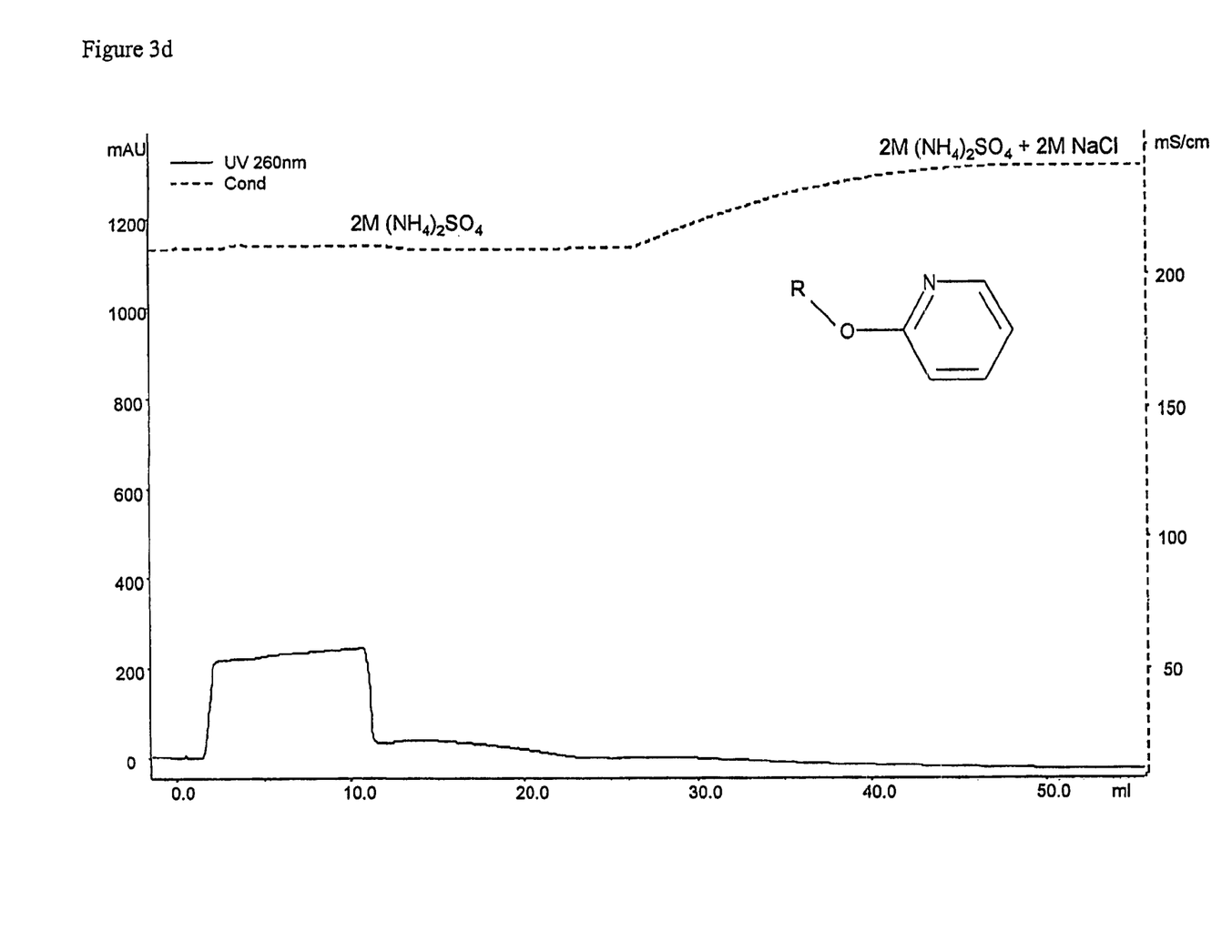
Figure 3E:
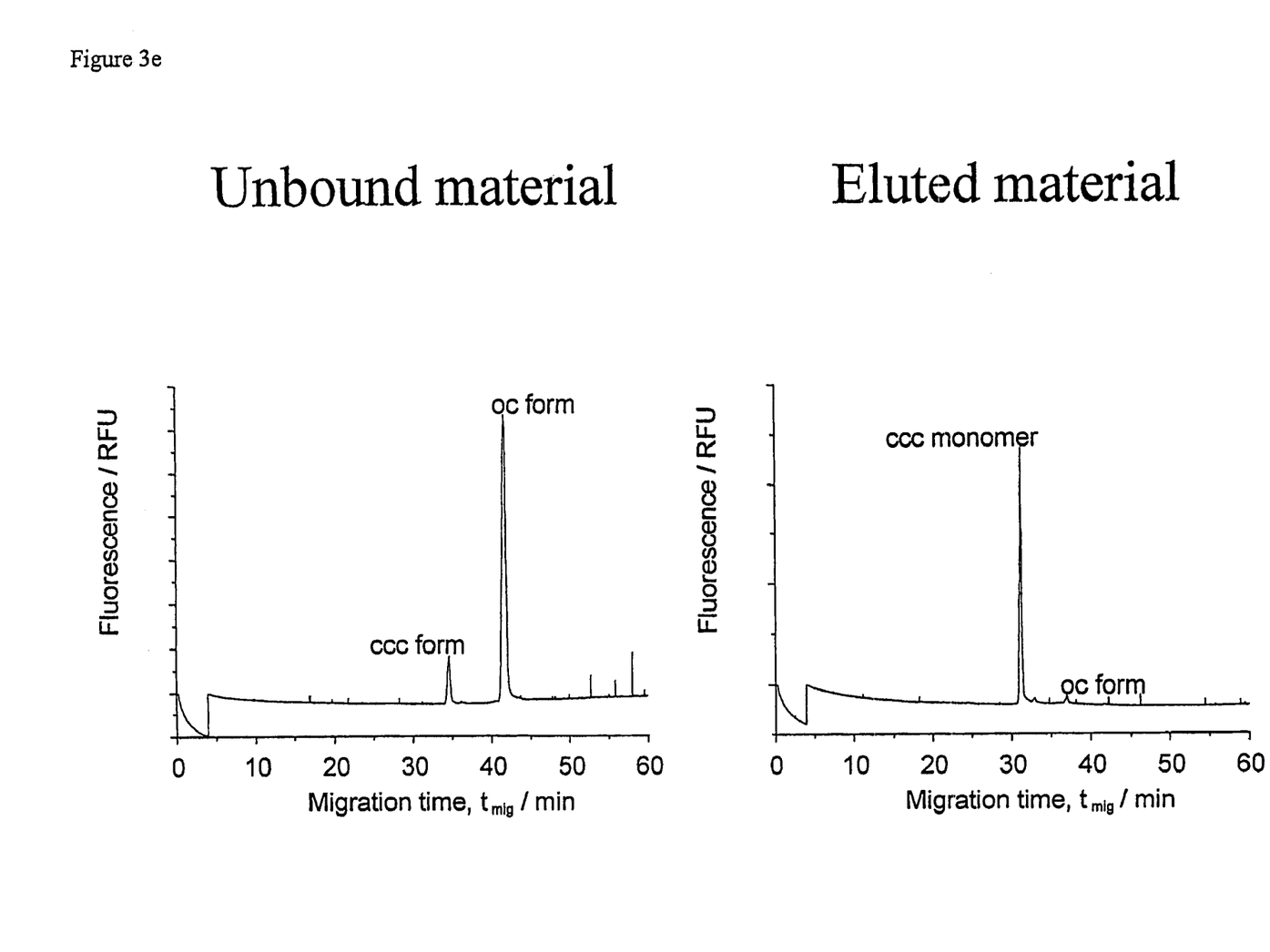
FIG. 3e shows electropherograms after laser induced fluorescence capillary gel electrophoresis of samples obtained after chromatography on aromatic thioether ligands.

FIGS. 3a and 3b illustrate the purification of supercoiled plasmid DNA on different columns with aromatic thioether ligands according to the invention. The plasmid DNA sample is prepared as in FIG. 2 and loaded on a column preconditioned in 2.0 M $(NH_4)_2SO_4$, 10 mM EDTA, 100 mM Tris-HCl, pH 7.0. Desorption of the supercoiled plasmid DNA is obtained with a gradient to 2M NaCl in the same buffer. Under these conditions, open circular plasmid DNA does not bind to the matrix, while supercoiled plasmid DNA binds and can be eluted by increasing NaCl-concentration. FIGS. 3c and 3d are comparative examples of similar ligands, that however, are either not aromatic (FIG. 3c) or have no thioether present (FIG. 3d). The experiments are run with the same sample and buffers as in FIGS. 3a and 3b. It is clear from the chromatograms that none of these last-mentioned ligands are suited for the type of chromatography described in FIG. 3a and FIG. 3b. FIG. 3e depicts electropherograms after laser induced fluorescence capillary gel electrophoresis of samples obtained in experiments analogous to FIG. 3a. Open circular form of plasmid DNA was not retained by the aromatic thioether ligand, while supercoiled forms of the plasmid were adsorbed and eluted early in the linear gradient.

Figure 4:
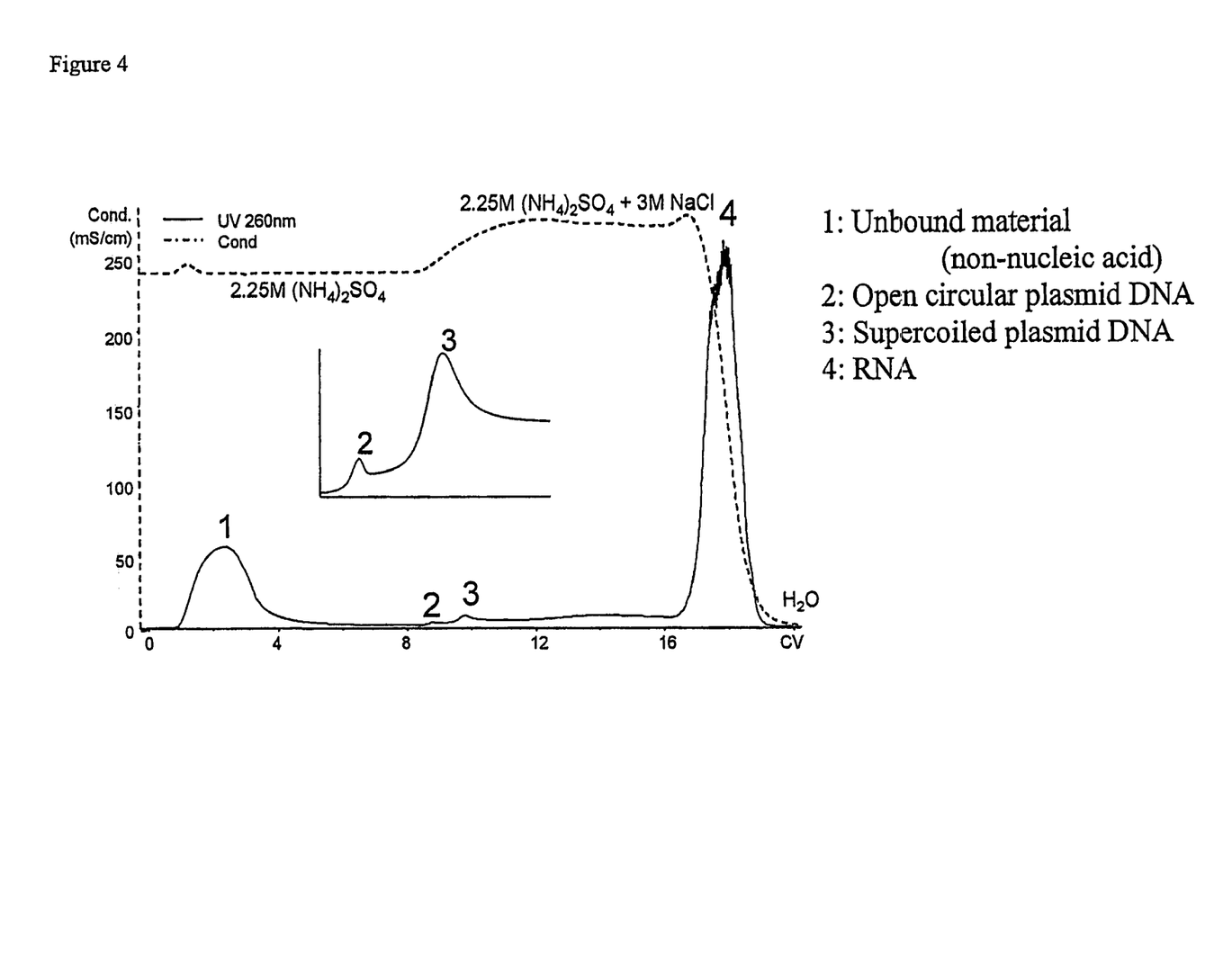
FIG. 4 is a chromatogram illustrating binding of clarified alkaline lysate on an aromatic thioether ligand and elution of the different nucleic acid fractions.

FIG. 4 illustrates adsorption and desorption of alkaline lysate to a thiophilic aromatic-chromatography matrix. The clarified alkaline lysate sample is diluted with 4M M $(NH_4)_2SO_4$, 10 mM EDTA, 100 mM Tris-HCl, pH 7.0 to obtain a final concentration of 2.25M $(NH_4SO_4)$. In 2.25 M $(NH_4)_2SO_4$, 10 mM EDTA, 100 mM Tris-HCl, pH 7.0, all nucleic acid molecules adsorb to the matrix. Desorption is however different for the different nucleic acids. Isoforms of the plasmid DNA can be separated by a gradient to 3 M NaCl in the 2.25 M $(NH_2)_2SO_4$, 10 mM EDTA, 100 mM Tris-HCl, pH 7.0 buffer (insert at higher magnification), while RNA can only be eluted from the matrix with a gradient to less $(NH_4)_2SO_4$, resulting in a complete and robust separation of the different types of nucleic acid molecules.

Figure 5:
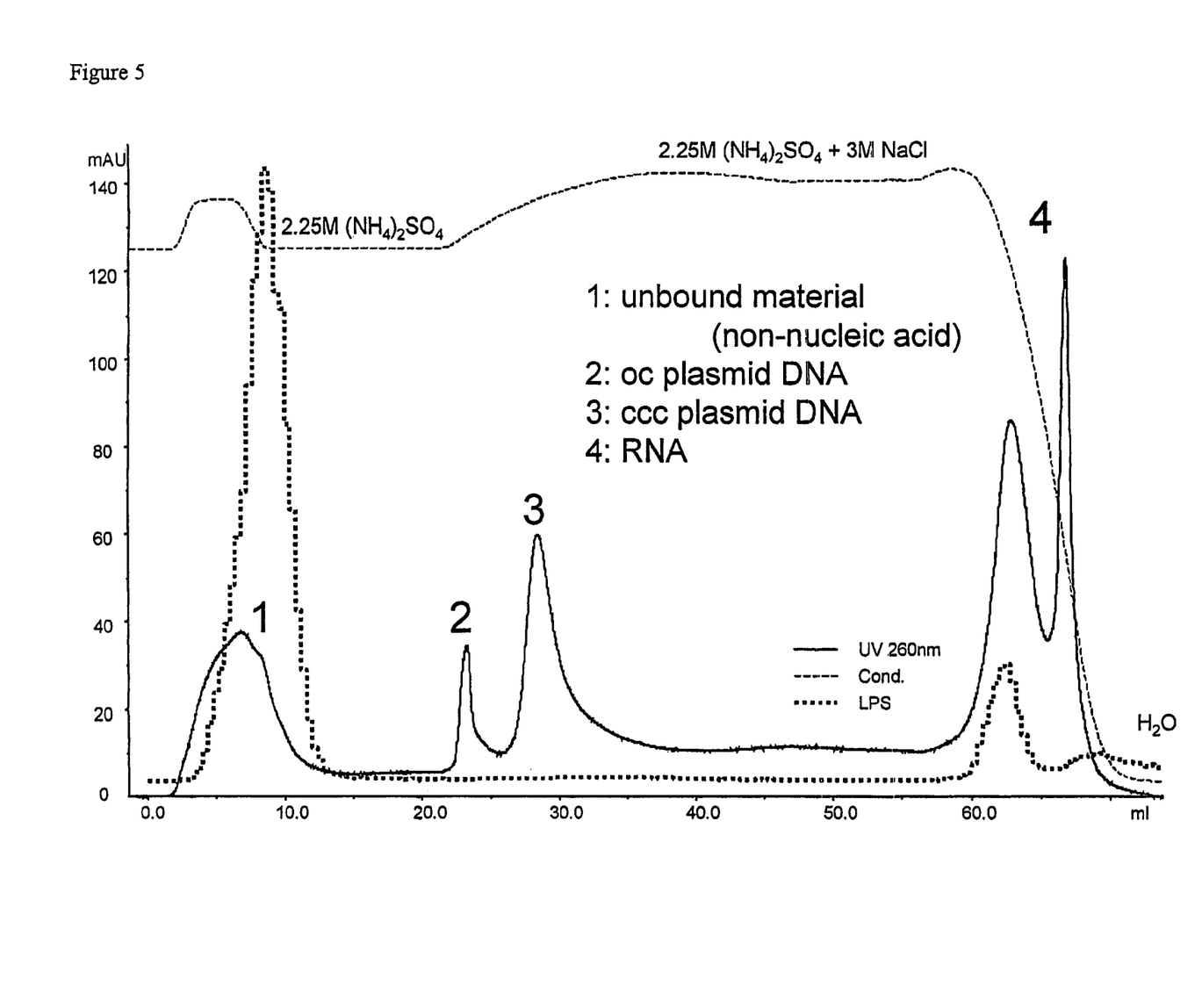
FIG. 5 is a chromatogram depicting the profile of plasmid DNA, RNA and lipopolysaccharides after chromatography on an aromatic thioether ligand.

FIG. 5 depicts the separation between plasmid DNA and lipopolysaccharides (LPS). Plasmid DNA is spiked with RNA and fluorescent LPS and loaded on 2-mercaptopyridine Sepharose™ 6 Fast Flow (Amersham Biosciences, Uppsala, Sweden) equilibrated in 2.25 M $(NH_4)_2SO_4$, 10 mM EDTA, 100 mM Tris-HCl, pH 7.0. Plasmid DNA isoforms elute by increasing the conductivity in a gradient to 3M NaCl in equilibration buffer, while RNA and LPS elute by decreasing the conductivity by a gradient to water.

Figure 6:
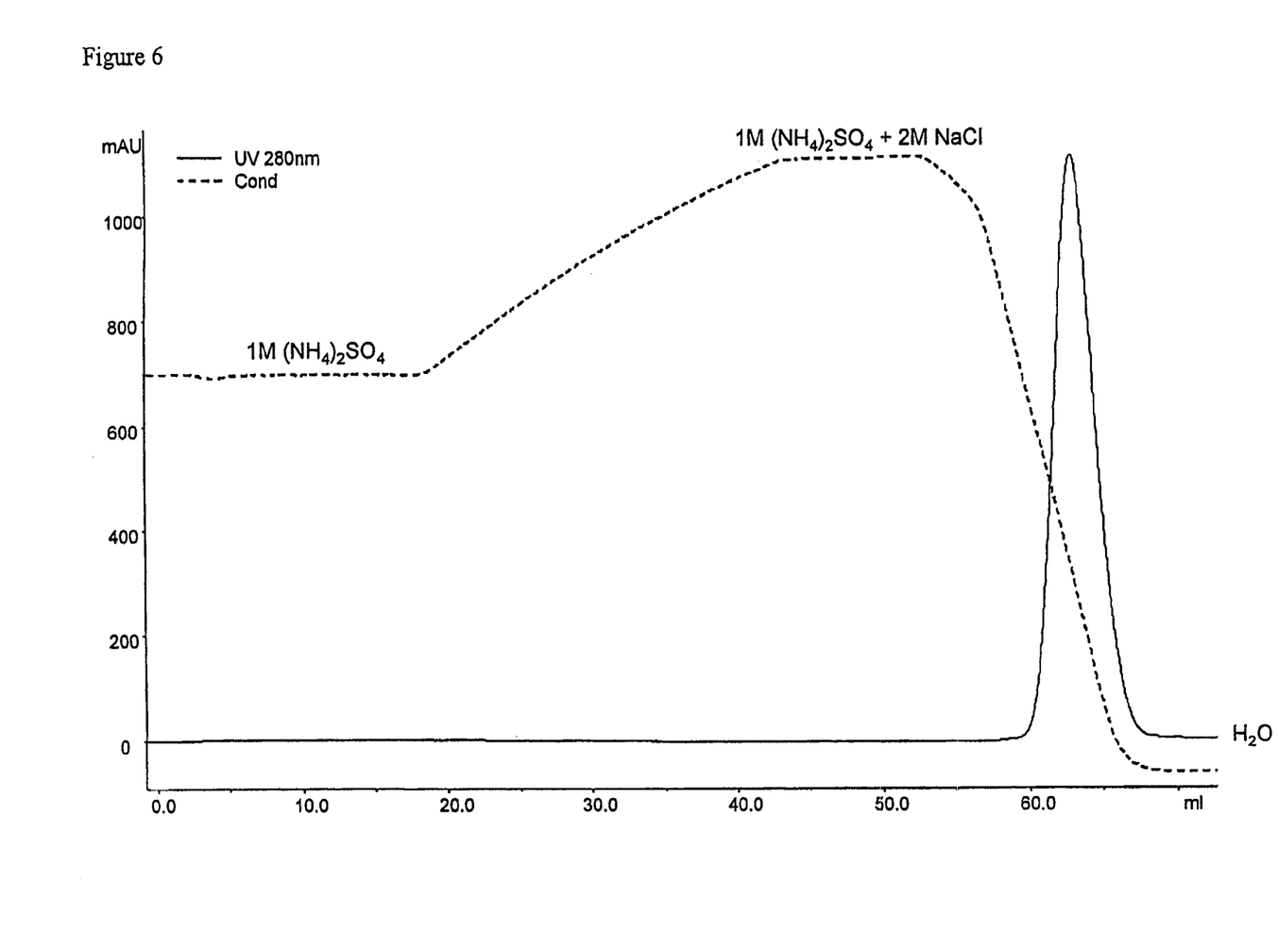
FIG. 6 shows the result obtained after chromatography of immunoglobulins on an aromatic thioether ligand.

FIG. 6 shows how immunoglobulins can adsorb to 2-mercaptopyridin Sepharose™ 6 Fast Flow (Amersham Biosciences, Uppsala, Sweden) in 1.0 M $(NH_4)_2SO_4$, 10 mM EDTA, 100 mM Tris-HCl, pH 7.0. They can however not be eluted by increasing the conductivity with NaCl. For desorbing the proteins, conductivity has to be decreased by lowering the $(NH_4)_2SO_4$-concentration. This indicates a hydrophobic binding principle, different from the binding mechanism for nucleic acid molecules to the aromatic thioether-type ligand used according to the invention.

Figure 7:
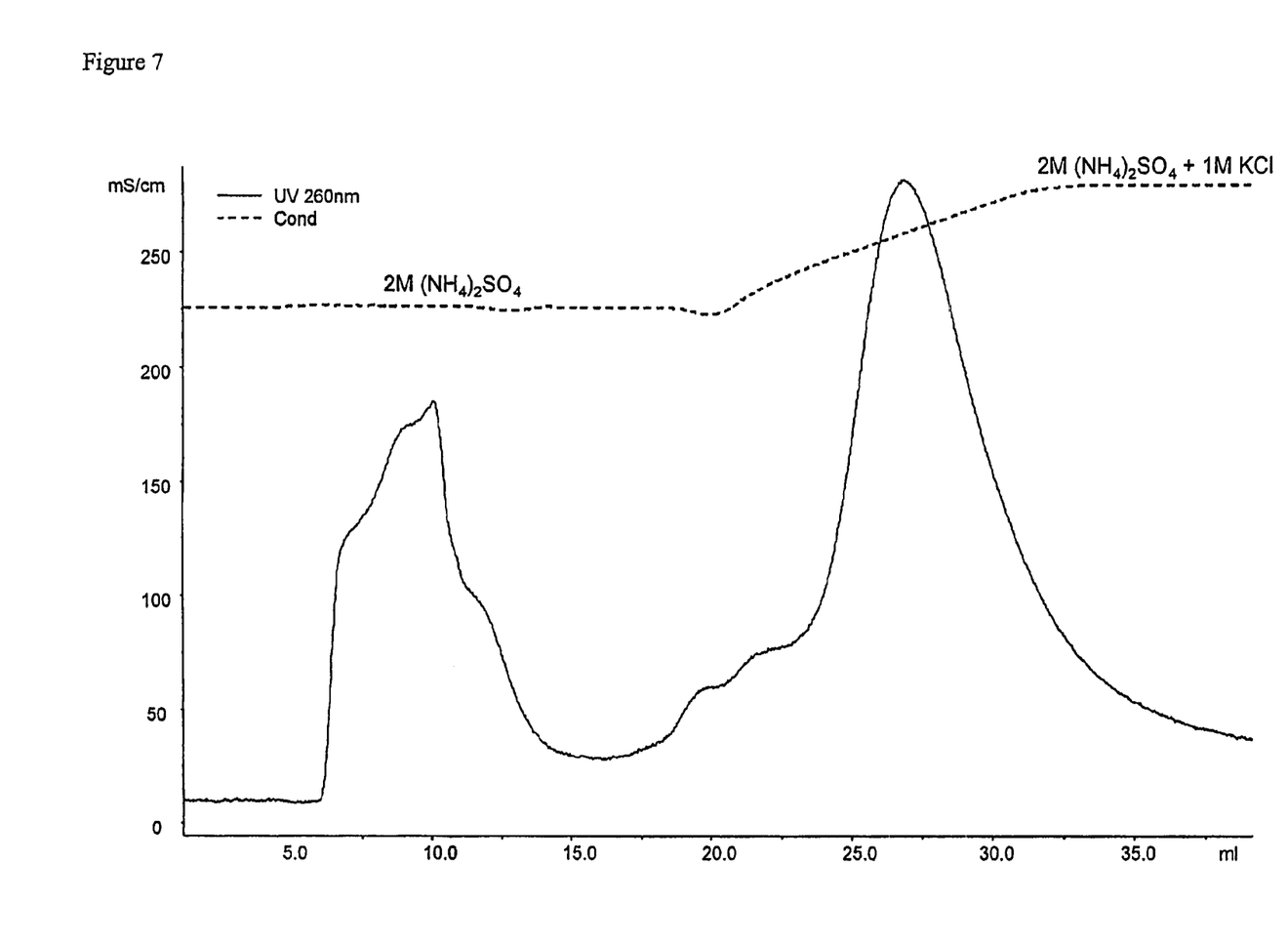
FIG. 7 is a chromatogram illustrating elution of plasmid DNA by an increasing KCl gradient

FIG. 7 shows that other salts for eluting the plasmid DNA molecules can replace NaCl. Plasmid DNA, prepared as in FIG. 2 is loaded on 2-mercaptopyridin Sepharose™ 6 Fast Flow (Amersham Biosciences, Uppsala, Sweden) in 2.0 M $(NH_4)_2SO_4$, 10 mM EDTA, 100 mM Tris-HCl, pH 7.0 and eluted with a gradient to 1M KCl in loading buffer.

Figure 8:
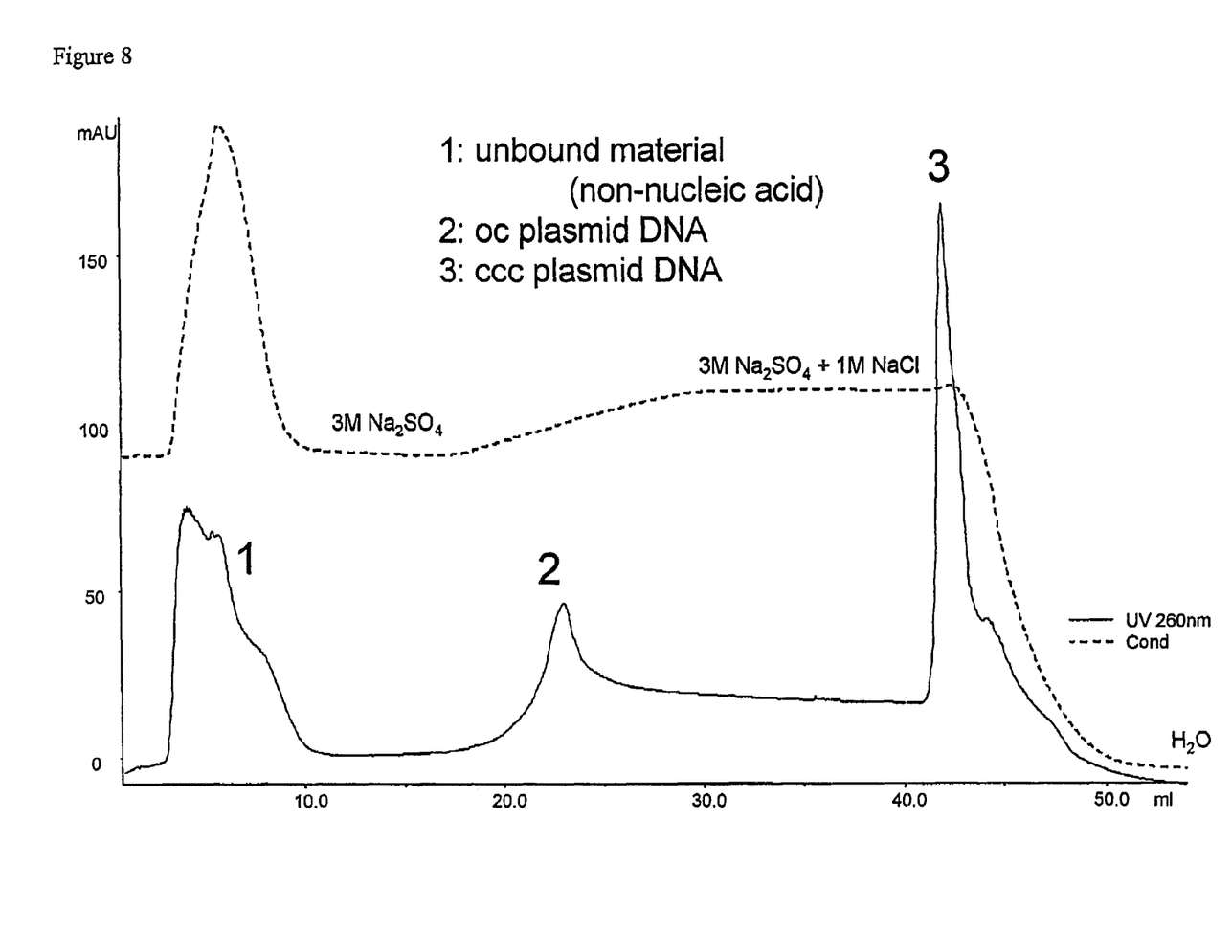
FIG. 8 is a chromatogram demonstrating the use of $Na_2SO_4$ as lyotropic salt for the purification of plasmid DNA on aromatic thioether ligands.

FIG. 8 illustrates how plasmid DNA is loaded on a column preconditioned in 3.0 M $Na_2SO_4$, 10 mM EDTA, 100 mM Tris-HCl, pH 7.0 and eluted with a gradient to 1M NaCl in the buffer used for preconditioning. Thus, the figure demonstrates the replacement of the hydrophobic salt used for binding of nucleic acid molecules to the thiophilic aromatic chromatography matrix.

Figure 9A:
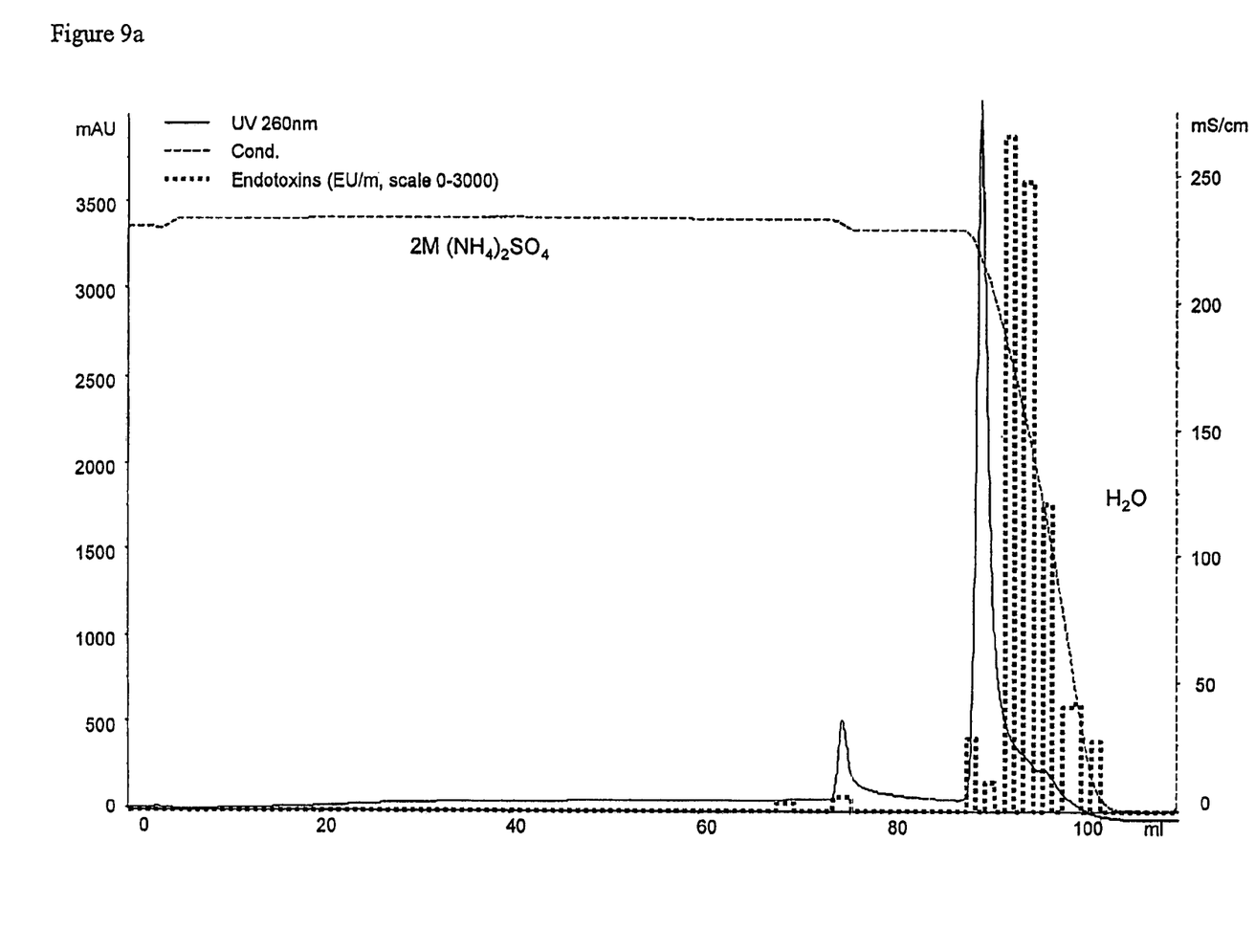
Figure 9B:
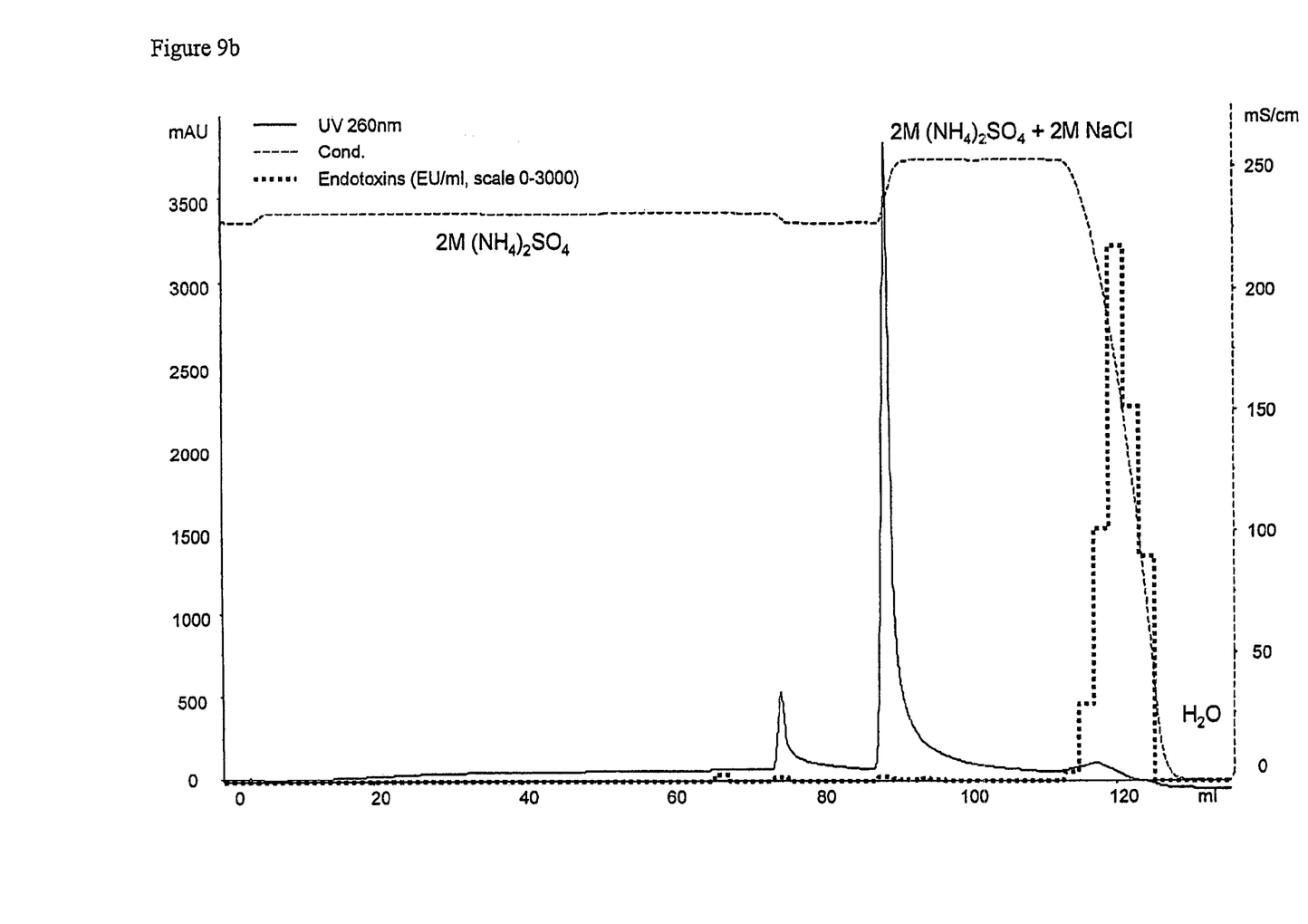

FIGS. 9a and b illustrate the differences in endotoxin profile when eluting from an aromatic thioether ligand used according to the invention with either decreasing or increasing salt concentration. Plasmid DNA is prepared as in FIG. 2 and loaded on 2-mercaptopyridin Sepharose™ 6 Fast Flow (Amersham Biosciences, Uppsala, Sweden) at 2.0 M $(NH_4)_2SO_4$, 10 mM EDTA, 100 mM Tris-HCl, pH 7.0. Consequently supercoiled plasmid DNA is eluted with either a gradient to water (FIG. 9a) or a gradient to 2M NaCl, 2.0 M $(NH_4)_2SO_4$, 10 mM EDTA, 100 mM Tris-HCl, pH 7.0 followed with a gradient to water (FIG. 9b). Some fractions were tested for endotoxin content using the standard LAL-test. From the experiment it is clear that the major bulk of endotoxins elute when decreasing the conductivity. Consequently, supercoiled plasmid DNA is preferably eluted by increasing the conductivity. In this manner, the supercoiled plasmid DNA is eluted and can be collected without co-elution of endotoxins.

Experimental Part

Below the present invention will be disclosed by way of examples, which are intended solely for illustrative purposes and should not be construed as limiting the present invention as defined in the appended claims. All references mentioned below or elsewhere in the present application are hereby included by reference.

Chromatograph Media Prototypes

All ligands (inserts in FIG. 2a to 2d) were coupled to epoxy-activated Sepharose™ 6 Fast Flow (Amersham Biosciences, Uppsala, Sweden) by established methods (Hermanson, G. T., Mallia, A. K. & Smith, P. K. *Immobilised affinity ligand techniques*. Academic Press Limited, London, 1992, p. 51-132). The ligand concentration was chosen to be in excess over available binding sites and after washing, the amount of coupled ligand was checked by elemental analysis (sulphur or nitrogen).

Plasmid DNA

A 6125 base pair plasmid composed of pUC19 plasmid with an insert representing part of protein A (the identity of the insert is not important here) was used for this study. The plasmid was transfected and grown in *E. coli* TG1α by well-established protocols (Sambrook, J., and Russel, D. W. *Molecular cloning: a laboratory manual*, Cold Spring Harbor, N.Y., 2001). Clarified alkaline lysate was prepared according to Horn et al. (Horn, N. A, Meek, J. A., Budahazi, G., and Marquet, M. Cancer gene therapy using plasmid DNA: purification of DNA for human clinical trials. *Human Gene Therapy* 1995; 6, 565-573). A crude plasmid DNA preparation (containing both open circular and supercoiled isoforms) was prepared and used in FIG. 2. 1 litre of clarified alkaline lysate, was loaded on Sepharose™ 6 Fast Flow (Amersham Biosciences, Uppsala, Sweden) packed in an INdEX™ 100 column (Amersham Biosciences) at 30 cm/h in order to change the buffer to the desired $SO_4^{2-}$-concentration in 10 mM EDTA, 100 mM Tris-HCl, pH 7.0 (2.0M $(NH_4)_2SO_4$ in FIGS. 3, 7 and 9; 2.25M $(NH_4)_2SO_4$ in FIGS. 4 and 6; 3.0M $Na_2SO_4$ in FIG. 8). Simultaneously, this procedure also removed RNA and other contaminants (not shown).

Chromatographic Procedures

All column chromatography was performed with an ÄKTA™ explorer (Amersham Biosciences) at 75 cm/h. Samples were loaded on columns preconditioned in the appropriate $SO_4^{2-}$-concentration in 10 mM EDTA, 100 mM Tris-HCl, pH 7.0 (1.0M $(NH_4)_2SO_4$ in FIG. 5; 2.0M $(NH_4)_2SO_4$ in FIGS. 3, 7 and 9; 2.25M $(NH_4)_2SO_4$ in FIGS. 4 and 6; 3.0M $Na_2SO_4$ in FIG. 8) and eluted with a gradient to salt in the same buffer (2M NaCl in FIG. 3a-d, 3M NaCl in FIGS. 4, 5, 6, 8 and 9b, 1M KCl in FIG. 7) or to water (FIG. 9a) in 10 (FIGS. 3, 5 and 6) or 5 (FIGS. 4, 7, 8 and 9a-b) column volumes. In FIGS. 4, 5, 6, 8 and 9b, the salt gradient is followed by a water gradient for complete removal of contaminants.

Fluorescent-Lipopolysaccharides

To estimate the elution profile of endotoxins in the chromatographic method, five ml of a sample containing the different plasmid DNA isoforms was spiked with RNA and 2.5 µg/ml of a fluorescently labelled 10.000 Da lipopolysaccharide isoform from *E. coli* (Isotype 055:B5, Molecular Probes, Leiden, The Netherlands). Fractions were collected and fluorescence was recorded according to the manufacturers' instructions.

Analytical Procedures

Peaks 1, 2, 3 and 4 in FIGS. 4 and 5 were judged to be non-nucleic acid, open circular plasmid DNA, supercoiled plasmid DNA and RNA respectively by their 260 nm/280 nm absorption ratios and their electrophoretic mobility pattern on 1% agarose gel electrophoresis and ethidium bromide staining (Sambrook, J., and Russel, D. W. *Molecular cloning: a laboratory manual*, Cold Spring Harbor, N.Y., 2001) (not shown).

Endotoxin values were determined with the standard LAL-test according to the manufacturer's instructions.

Laser induced fluorescence capillary gel electrophoresis was performed as described by Schmidt et al. (Schmidt, T., Friehs, K, and Flaschel, E. (2001): *Structures of plasmid DNA*, in: M. Schleef (Ed.): "*Plasmids for therapy and vaccination*", pp. 29-43, Wiley-VCH, Weinheim).

What is claimed is:

1. A method of separating nucleic acid molecules from contaminants in a solution and isolating one or more desired nucleic acid molecules, which method comprises the following steps
    (a) providing an aqueous adsorption solution, which includes nucleic acids and a salt that forms lyotropic ions when dissolved;
    (b) passing said solution over a matrix to adsorb the nucleic acids onto the matrix, said matrix including an aromatic ring moiety and at least one thioether moiety;
    (c) passing an aqueous eluent over said matrix to desorb the nucleic acid molecules therefrom, which eluent includes a salt that forms lyotropic ions and a gradient of increasing ionic strength originating from an increasing concentration of a salt that forms less lyotropic ions when dissolved than the ones present in said aqueous adsorption solution; and
    (d) isolating a fraction comprising the desired nucleic acid molecules.

2. The method of claim 1, wherein the fraction isolated is plasmid DNA, which is essentially free from proteineous components and/or RNA and/or endotoxins.

3. The method of claim 1, wherein the lyotropic and less lyotropic ions of steps (a) and (c) are anions formed of the respective salts.

4. The method of claim 1, wherein the salt in step (a) is ammonium sulphate or sodium sulphate.

5. The method of claim 4, wherein the salt in the adsorption solution is at a concentration below about 3 M.

6. The method of claim 1, wherein the salt dissolved in the eluent is an alkali salt, such as sodium chloride or potassium chloride.

7. The method of claim 6, wherein the salt in the eluent is at a concentration no greater than about 3 M.

8. The method of claim 1, wherein the matrix is comprised of a carrier to which an aromatic thioether ligand has been coupled, wherein in said ligand the aryl group is selected from the group consisting of pyridyl, phenyl, benzyl, toluyl, phenethyl, naphtyl, imidazolyl, pyrazolyl, pyrazinyl, pyrimidinyl, pyridazinyl, piperidinyl, morpholinyl, piperazinyl, indolyl, quinolinyl, and purinyl groups.

9. The method of claim 8, wherein the ligand has been coupled to the carrier via the thioether moiety.

10. The method of claim 1, further comprising the step of washing said matrix after step (b).

\* \* \* \* \*